United States Patent [19]

Mathiesen et al.

[11] Patent Number: 5,087,241

[45] Date of Patent: Feb. 11, 1992

[54] IONTOPHORESIS ELECTRODE WITH RESERVOIR AND INJECTION SITE

[75] Inventors: George E. Mathiesen, Inver Grove Heights; Stacy D. Mattson, Anoka, both of Minn.

[73] Assignee: Empi, Inc., St. Paul, Minn.

[21] Appl. No.: 558,250

[22] Filed: Jul. 24, 1990

[51] Int. Cl.⁵ .................................................. A61N 1/30
[52] U.S. Cl. .................................... 604/20; 128/798; 128/803
[58] Field of Search ............... 604/20; 128/640, 641, 128/798, 802, 803

[56] References Cited

U.S. PATENT DOCUMENTS

| | | | |
|---|---|---|---|
| 3,610,229 | 10/1971 | Zenkich | 128/641 |
| 3,677,268 | 7/1972 | Reeves | 128/172.1 |
| 3,848,600 | 11/1974 | Patrick, Jr. et al. | 128/303.13 |
| 3,991,755 | 11/1976 | Vernon et al. | 128/172.1 |
| 4,140,122 | 2/1979 | Kuhl et al. | 128/260 |
| 4,141,359 | 2/1979 | Jacobsen et al. | 128/172.1 |
| 4,166,457 | 9/1979 | Jacobsen et al. | 128/639 |
| 4,215,696 | 8/1980 | Bremer et al. | 128/641 |
| 4,250,878 | 2/1981 | Jacobsen et al. | 128/207 |
| 4,292,968 | 10/1981 | Ellis | 128/207 |
| 4,383,529 | 5/1983 | Webster | 604/20 |
| 4,406,658 | 9/1983 | Lattin et al. | 604/20 |
| 4,416,274 | 11/1983 | Jacobsen et al. | 604/20 |
| 4,419,092 | 12/1983 | Jacobsen et al. | 604/20 |
| 4,465,074 | 8/1984 | Buchalter | 128/639 |
| 4,474,570 | 10/1984 | Ariura et al. | 604/20 |
| 4,477,972 | 10/1984 | Jacobsen et al. | 28/877 |
| 4,526,176 | 7/1985 | Bremer et al. | 128/641 |
| 4,557,723 | 12/1985 | Sibalis | 604/20 |
| 4,570,637 | 2/1986 | Gomes et al. | 128/639 |
| 4,602,909 | 7/1986 | Csillik et al. | 604/20 |
| 4,639,244 | 1/1987 | Rizk et al. | 604/19 |
| 4,689,039 | 8/1987 | Masaki | 604/20 |
| 4,700,710 | 10/1987 | Hoffman | 128/802 X |
| 4,713,050 | 12/1987 | Sibalis | 604/20 |
| 4,722,726 | 2/1988 | Sanderson et al. | 604/20 |
| 4,731,049 | 3/1988 | Parsi | 604/20 |
| 4,744,787 | 5/1988 | Phipps et al. | 604/20 |
| 4,747,819 | 5/1988 | Phipps et al. | 604/20 |
| 4,752,285 | 6/1988 | Petelenz et al. | 604/20 |
| 4,767,401 | 8/1988 | Siederman | 604/20 |
| 4,820,263 | 4/1989 | Spevak et al. | 604/20 |
| 4,822,339 | 4/1989 | Tran | 604/82 |
| 4,842,577 | 6/1989 | Konno et al. | 604/20 |
| 4,846,179 | 7/1989 | O'Connor | 128/419 |
| 4,856,188 | 8/1989 | Sibalis | 29/877 |
| 4,865,582 | 9/1989 | Sibalis | 604/20 |
| 4,878,892 | 11/1989 | Sibalis et al. | 604/20 |
| 4,883,457 | 11/1989 | Sibalis | 604/20 |
| 4,883,668 | 11/1989 | Ohta | 424/448 |
| 4,911,688 | 3/1990 | Jones | 604/20 |
| 4,926,878 | 5/1990 | Snedeker | 128/798 |
| 4,968,297 | 11/1990 | Jacobsen et al. | 604/20 |

*Primary Examiner*—Lee S. Cohen
*Attorney, Agent, or Firm*—Kinney & Lange

[57] ABSTRACT

An iontophoresis electrode configured for positioning on a patient's skin during a drug treatment. The electrode includes a flexible backing layer having a first surface with an adhesive layer for holding the electrode together and for securing the electrode to the skin. A conductive material layer adheres to the adhesive layer. An absorbent pad layer, positioned adjacent the conductive material layer, holds a drug solution during the treatment. A dispersive material layer overlies the absorbent pad layer to disperse the solution evenly about a skin-electrode interface. The dispersive material layer and the flexible backing layer enclose the conductive material layer and the absorbent pad layer. A plurality of radially oriented slits extend through the conductive material layer at an aperture in the adhesive backing layer to form a site at which the drug solution can be injected into the absorbent pad layer. A snap-type electrical contact is attached to the conductive material layer.

33 Claims, 2 Drawing Sheets

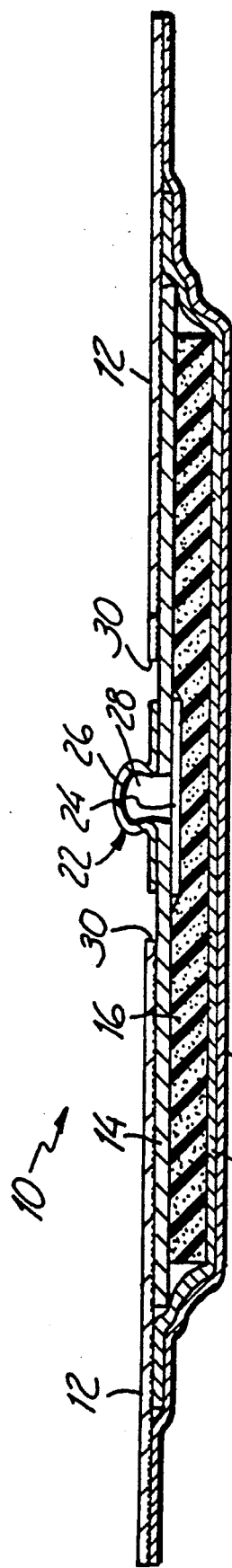
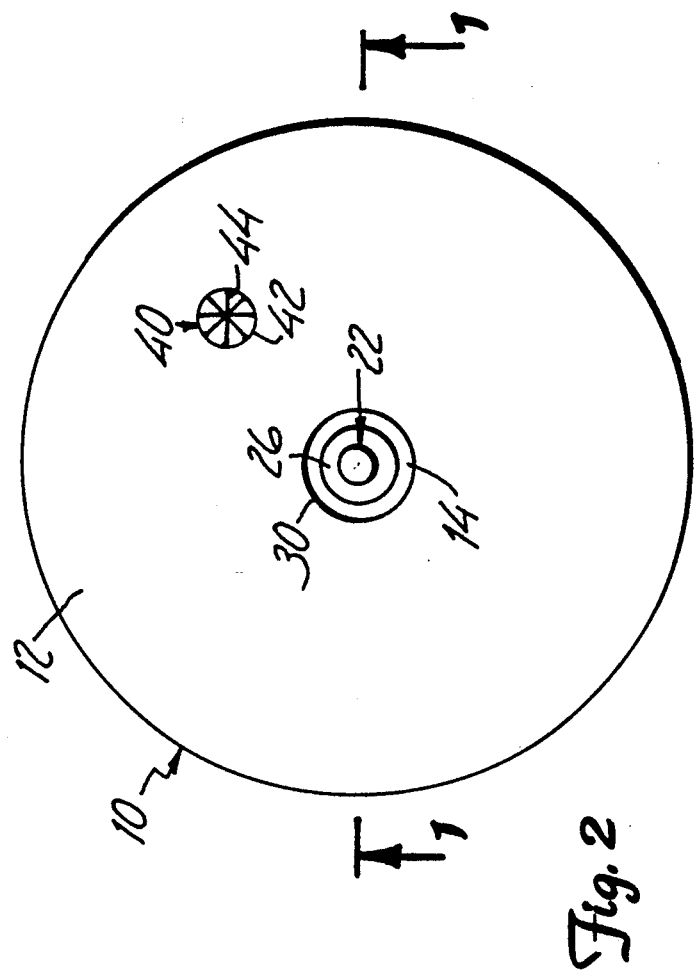

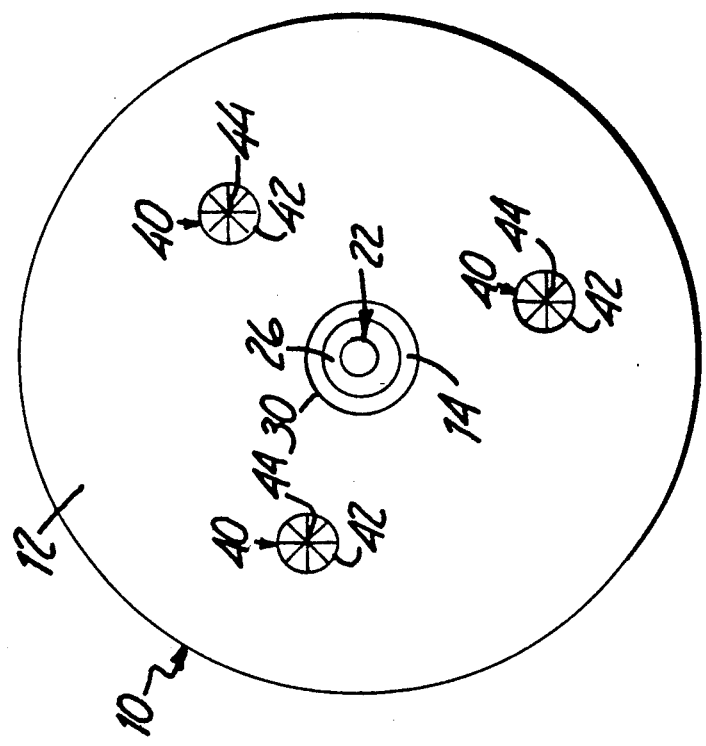

IONTOPHORESIS ELECTRODE WITH RESERVOIR AND INJECTION SITE

BACKGROUND OF THE INVENTION

The present invention relates to an electrode for use in iontophoresis therapy. In particular, the present invention relates to an iontophoresis electrode having a drug solution injection site and a reservoir for holding the solution during a treatment.

There is an ongoing search for methods of medical treatment which are non-invasive and painless. An effective treatment is useless if the patient refuses it due to the pain it can cause. Iontophoresis medication delivery systems are safe, effective, non-invasive, and relatively painless.

Iontophoresis involves the interaction between ionized molecules of a drug and an external electric field, resulting in the migration of charged molecules. The migration is achieved by placing two electrodes on the patient's skin which are connected to an electric DC power supply. One of the electrodes is an "active" electrode filled with a drug solution. The other electrode is an "inactive" or "indifferent" electrode filled with an electrolyte solution. The electric field generated between the two electrodes causes the charged drug molecules to migrate from the active electrode into the tissues and blood stream of the patient without the necessity of hypodermic injection and its adverse effects, such as pain and risk of infection.

Delivery of drugs via iontophoresis also presents the advantage of avoiding first-pass metabolism of the drug. When a drug is taken orally and absorbed from the digestive tract into the blood stream, the blood containing the drug first percolates through the liver, a metabolically active organ, before entering the general circulation for delivery to the target tissue. Thus, much of the orally ingested drug may be metabolically inactivated before it has a chance to exert its pharmacologic effect. Local delivery of drugs, therefore, presents advantages over oral administration, an application characterized by inefficiency and unpredictability, and over hypodermic injection, an invasive, inconvenient, and sometimes risky technique.

One factor that controls the effectiveness of iontophoresis is the design of the active, or drug delivery, electrode. Preferably, the drug delivery electrode includes an injection site that allows insertion of the drug solution before or during a treatment session. In this manner, the electrode may be stored, prior to treatment, in a "dry" state for an extended period of time without the risk of evaporation or leakage. The electrode should readily adhere to the patient's skin during treatment and should be flexible to facilitate a variety of electrode placements. The electrode should hold a volume of solution sufficient for the individual treatment session and should hold the solution for the allotted treatment time. Finally, the electrode should provide an adequate conductive surface area to prevent burning of the patient's skin.

Because the drug delivery electrodes are typically discarded after a single treatment session, these electrodes should therefore be of very low cost. However, drug delivery electrodes of the prior art typically include a plastic or rubber housing that forms a reservoir to hold the drug solution. Unfortunately, these housings are relatively expensive to manufacture. Thus, disposing each electrode after a single use becomes expensive. Even further, these housings are relatively stiff and do not adequately conform to the surface of the patient's skin during treatment. As a result, an inexpensive, flexible electrode having a low-profile is desired.

SUMMARY OF THE INVENTION

The present invention is an electrode for use in iontophoresis drug therapy. The electrode enables the safe, effective, non-invasive, and relatively painless delivery of medication across the skin of a patient. The electrode is inexpensive, has a low-profile, and is sufficiently flexible to conform to the patient's skin.

The electrode includes a flexible backing layer having a first surface with an adhesive layer for holding the electrode together and for securing the electrode to the skin. A conductive material layer adheres to the adhesive layer. An absorbent pad layer positioned adjacent the conductive material layer holds a given volume of drug solution during the treatment. A thin, dispersive material layer overlies the absorbent pad layer and disperses the solution evenly about a skin-electrode interface. The dispersive material layer and the flexible backing layer enclose the conductive material layer and the absorbent pad layer. A plurality of radially oriented slits extend through the conductive material layer at an aperture in the adhesive backing layer to form a site at which the drug solution can be injected into the absorbent pad layer. An electrical contact is attached to the conductive material layer to provide a connection for coupling the electrode to a power supply.

In a preferred embodiment, the electrode further includes a removable protective layer that overlies the dispersive material layer and the adhesive layer. The removable protective layer is peeled off of the adhesive layer to allow attachment of the electrode to the patient's skin prior to the treatment session. The electrode can also include a plurality of injection sites to ensure a more even distribution of solution within the absorbent pad layer.

The electrical contact is preferably a snap with an eyelet and a stud positioned on opposite faces of the conductive material layer. The stud includes a post that extends through the conductive material layer and connects with the eyelet. Preferably, the eyelet includes conductive material and the stud includes nonconductive material.

BRIEF DESCRIPTION OF THE DRAWINGS

FIG. 1 is a sectional view of an iontophoresis electrode in accordance with the present invention.

FIG. 2 is a top plan view of the iontophoresis electrode shown in FIG. 1.

FIG. 3 is a top plan view of an iontophoresis electrode having a plurality of injection sites in accordance with the present invention.

DETAILED DESCRIPTION OF THE PREFERRED EMBODIMENTS

FIG. 1 is a sectional view of an iontophoresis electrode 10 in accordance with the present invention. Electrode 10 is a low cost and easily manufactured electrode which can be conveniently used for iontophoresis drug therapy. The following discussion is made with reference to both FIG. 1 and FIG. 2. Common electrode elements are referred to by the same reference numerals in the figures.

Electrode 10 has a low-profile and is sufficiently flexible to conform to a variety of skin contours. Electrode 10 includes adhesive backing layer 12, conductive material layer 14, absorbent pad layer 16, dispersive layer 18, removable protective layer 20, electrical contact or snap 22, and drug solution injection site 40.

Adhesive backing layer 12 is an adhesive tape that serves as a structural support component of electrode 10, and also provides the means of attaching electrode 10 to the patient's skin. Adhesive backing layer 12 generally forms a "patch" that overlies the rest of the electrode's component parts and holds the electrode together against the patient's skin. Because adhesive backing layer 12 is highly flexible, it easily conforms to the patient's skin. Adhesive backing layer 12 also serves to prevent leakage of a drug solution contained in the electrode 10. In one embodiment, adhesive backing layer 12 includes a layer of polyvinyl chloride foam having a first or lower layer of medical grade acrylic pressure-sensitive adhesive. It is to be understood that other flexible materials having an adhesive layer may also be used as an adhesive backing layer in accordance with the present invention.

Conductive material layer 14 adheres to the adhesive layer of backing layer 12. Conductive material layer 14 conducts current applied to snap 22 and distributes the current evenly across absorbent pad layer 16. In one embodiment, conductive material layer 14 includes a sheet of carbon-loaded silicone rubber with a maximum resistivity of 10 ohms cm. Other materials, such as a thin sheet of metal foil, metal screen, wire mesh or highly conductive cloth, can also be used. These materials are flexible and have high conductivity so as to provide low current density and even current distribution in both lateral directions (i.e. width and length).

In one embodiment, adhesive backing layer 12 has a surface area that is approximately 4 inches square and conductive material layer 14 has a surface area that is approximately 1.77 inches square. However, these dimensions may be varied widely within the scope of the present invention.

Absorbent pad layer 16 is positioned adjacent to and contacts conductive material layer 14. Absorbent pad 16 accepts the drug solution from injection site 40 and holds the solution during the treatment session. In one embodiment, absorbent pad 16 includes 100% polyester fiber fill. However, other porous, flexible materials can also be used as an absorbent pad within the scope of the present invention.

Dispersive material layer 18 overlies conductive material layer 14 and absorbent pad layer 16. The perimeter of dispersive layer 18 extends beyond the perimeter of absorbent pad 16 and the perimeter of conductive material layer 14 such that the periphery of dispersive layer 18 contacts and adheres to adhesive backing layer 12. In this configuration, adhesive backing layer 12 and dispersive layer 18 fully enclose conductive material layer 14 and absorbent pad layer 16. Dispersive layer 18 is a highly wetable layer that draws the drug solution from absorbent pad layer 16 and evenly disperses the solution at the skin/electrode interface Dispersive layer 18 directly contacts the patient's skin during the treatment session to ensure uniform contact of the drug solution with the skin/electrode interface. Ionic interaction occurs through dispersive material layer 18. In one embodiment, dispersive material layer 18 includes a sheet of filter paper formed by an absorbent, low-particle polyester-cellulose.

During use, absorbent pad layer 16 and dispersive layer 18 together form a reservoir that holds a sufficient volume of drug solution for an individual treatment session. In one embodiment, the reservoir holds approximately 2 cc of solution. It to be understood that the dimensions of the electrode 10 may be varied within the scope of the present invention to vary its solution holding capacity.

Removable protective layer 20, a release liner, overlies dispersive layer 18 and adheres to adhesive backing layer 12. Protective layer 20 has a size and shape such that it substantially covers adhesive backing layer 12. Protective layer 20 protects electrode 10 during storage from possible contamination, and also prevents electrode 10 from adhering to undesirable surfaces during storage. Prior to use, protective layer 20 is peeled off to expose the adhesive about the outer periphery of backing layer 12 so that electrode 10 may be attached to the patient's skin surface. Protective coating layer 20 has a first surface in contact with backing layer 12 which can include a silicone layer to facilitate detachment from the backing layer.

Snap 22 provides a reliable mechanical and electrical connection between electrode 10 and a power source lead wire (not shown). Snap 22 includes stud 24 and eyelet 26. Stud 24 includes post 28 which extends through conductive layer 14 and mates with eyelet 26. Eyelet 26 is crimped around post 28 to hold eyelet 26 and stud 24 together on conductive layer 14. Stud 24 and eyelet 26 may be joined together using a conventional rivet type snap connector forming apparatus.

The lead wire (not shown) that is electrically coupled to the power supply (also not shown) may be easily snapped into and out of engagement with snap contact 22. Although snap contact 22 represents the preferred form of an electrical contact to conductive material layer 14, other forms of electrical contacts may also be used. For example, in another embodiment a pig tail electrical contact is used. Snap contact 22 is preferred, however, because of the ease of assembly and the rugged integral structure which is achieved.

Adhesive backing layer 12 includes aperture 30 having a diameter slightly larger than the diameter of eyelet 26. In this manner, eyelet 26 makes direct electrical contact with a first surface of conductive material layer 14. In one embodiment, the stud 24 is made of a nonconductive material and the eyelet 26 is made of a conductive material. This arrangement ensures that current flows from eyelet 26 to conductive material layer 14 and spreads evenly across the conductive material layer, instead of concentrating at stud 24. Preferably, the snap stud is formed from nonconductive plastic and the snap eyelet is formed from #300 series stainless steel. However, it must be understood that other, similar materials can be used with the present invention.

Prior to an individual treatment session, a clinician fills the electrode reservoir with a selected drug solution through injection site 40 (shown in FIG. 2). Injection site 40 is configured to accept the tip of a syringe barrel (not shown) with its needle removed. Injection site 40 is formed by an aperture 42 in adhesive backing layer 12 and by a plurality of radially oriented slits 44 through conductive material layer 14. Slits 44 generally form the shape of an asterisk coincident with aperture 42. In one embodiment, aperture 42 is formed by a generally cylindrical hole through adhesive backing layer 12. In another embodiment (not shown), slits 44 extend through both conductive material layer 14 and adhesive backing layer 12 to form aperture 42.

In one embodiment, injection site 40 is approximately 1 cm in diameter. Radial slits 44 form a plurality of flexible fingers that "open" upon the application of a given fluid pressure. This configuration allows the drug solution to be forced through conductive material layer 14 and into absorbent pad layer 16. Upon removal of the syringe tip, the fingers close preventing the drug solution from escaping through injection site 40 without excess pressure upon the drug-loaded electrode 10. In an alternative embodiment (shown in FIG. 3), electrode 10 includes a plurality of injection sites 40 to ensure even distribution of the drug solution within absorbent pad layer 16.

In another alternative embodiment (also not shown), conductive material layer 14, absorbent pad layer 16 and dispersive layer 18 each have portions that adhere to adhesive backing layer 12. Conductive material layer 14 is directly adjacent and adheres to adhesive backing layer 12. The perimeter of the absorbent pad layer 16 extends beyond the perimeter of conductive material layer 14 such that the periphery of the absorbent pad layer contacts and adheres to adhesive backing layer 12. The perimeter of the dispersive layer 18 extends beyond the perimeter of absorbent pad layer 16 such that the periphery of dispersive layer 18 contacts and adheres to adhesive backing layer 12. Finally, the perimeter of the protective layer 20 extends beyond the perimeter of dispersive layer 18 such that the periphery of protective layer 20 contacts and adheres to adhesive backing layer 12. Therefore, adhesive backing layer 12 provides structural support for each component part of electrode 10 but allows sufficient flexibility to conform to virtually any surface of the patient's skin.

In conclusion, the present invention provides a low-profile, disposable iontophoresis electrode that can be used on a single patient for one drug application. The electrode holds a sufficient volume of solution for the individual treatment session and provides an adequate conductive surface area to prevent burning of the patient's skin. The injection site allows insertion of the drug solution prior to, or during, the treatment session. In this manner, the electrode may be stored, prior to treatment, in a "dry" state for an extended period of time without the risk of evaporation or leakage.

The electrode readily adheres to the patient's skin during treatment and is sufficiently flexible to facilitate a variety of electrode placements. The flexible construction further allows for even distribution of the drug solution across the patient's skin to reduce current densities through the patient's skin. This results in a reduction of skin irritation and hence, an increase in patient comfort. The electrode's simple construction is relatively inexpensive to manufacture and assemble. The present invention therefore reduces the costs associated with iontophoresis drug therapy.

Although the present invention has been described with reference to preferred embodiments, workers skilled in the art will recognize that changes may be made in form and detail without departing from the spirit and scope of the invention.

What is claimed is:

1. An iontophoresis electrode configured for placement on a patient's skin during a drug treatment, the electrode comprising:
    a flexible backing layer having an aperture and a first surface, the first surface having an adhesive layer for holding the electrode together and for securing the electrode to the skin;
    a conductive material layer attached to the adhesive layer;
    an absorbent pad layer positioned adjacent the conductive material layer, the pad layer holding a drug solution;
    a thin, dispersive material layer which overlies the absorbent pad layer to disperse the solution evenly about a skin-electrode interface, wherein the dispersive material layer and the flexible backing layer enclose the conductive material layer and the absorbent pad layer;
    a plurality of radially oriented slits through the conductive material layer at the aperture in the flexible backing layer, the slits and aperture forming a site at which to inject the drug solution into the absorbent pad layer; and
    an electrical contact attached to the conductive material layer, the contact providing a connection for coupling to a power source.

2. The iontophoresis electrode of claim 1 wherein the flexible backing layer includes a sheet of adhesive tape.

3. The iontophoresis electrode of claim 2 wherein the flexible backing layer includes polyvinyl chloride foam.

4. The iontophoresis electrode of claim 2 wherein the adhesive layer includes medical grade acrylic pressure-sensitive adhesive.

5. The iontophoresis electrode of claim 1 wherein the conductive material layer includes carbon loaded silicone rubber.

6. The iontophoresis electrode of claim 5 wherein the conductive material layer has a maximum resistivity of 10 ohms-cm.

7. The iontophoresis electrode of claim 1 wherein the absorbent pad layer includes polyester fiber fill.

8. The iontophoresis electrode of claim 1 wherein the dispersive material layer includes a sheet of filter paper.

9. The iontophoresis electrode of claim 8 wherein the sheet of filter paper includes a sheet of absorbent low-particle polyester-cellulose.

10. The iontophoresis electrode of claim 1 wherein the aperture is formed by a generally cylindrical hole in the flexible backing layer.

11. The iontophoresis electrode of claim 1 wherein the aperture is formed by a plurality of radially oriented slits through the flexible backing layer that are substantially coincident with the slits through the conductive material layer.

12. The iontophoresis electrode of claim 1 wherein the electrode includes a plurality of injection sites.

13. The iontophoresis electrode of claim 1 and further comprising:
    a removable protective layer that overlies the dispersive material layer and the adhesive layer of the flexible backing layer.

14. The iontophoresis electrode of claim 1 wherein at least portions of the conductive material layer, the absorbent pad layer and the dispersive material layer adhere to the adhesive layer.

15. The iontophoresis electrode of claim 14 wherein:
    the conductive material layer has a perimeter; the absorbent pad layer has a perimeter which extends beyond the perimeter of the conductive material layer so that the absorbent pad layer adheres to the adhesive layer; and
    the dispersive layer has a perimeter which extends beyond the perimeter of the absorbent pad layer so that the dispersive layer adheres to the adhesive layer.

16. The electrode of claim 1 wherein the electrical contact includes a snap-type fastener mounted to the conductive material layer.

17. The iontophoresis electrode of claim 16 wherein the snap-type fastener includes an eyelet and a stud positioned on opposite faces of the conductive material layer, the stud having a post extending through the conductive material layer for connection with the eyelet.

18. The iontophoresis electrode of claim 17 wherein the eyelet includes conductive material and the stud includes nonconductive material.

19. The iontophoresis electrode of claim 16 wherein the flexible backing layer includes an aperture coincident with the snap-type fastener.

20. An iontophoresis electrode comprising:
a flexible adhesive tape layer having a first aperture and having a periphery for holding the electrode to the skin of a patient;
a conductive layer adhered to the adhesive tape layer;
an absorbent pad layer adjacent the conductive layer with a perimeter extending beyond a perimeter of the conductive layer so that the periphery of the absorbent pad layer adheres to the adhesive tape layer;
a thin, dispersive layer adjacent the absorbent pad layer with a perimeter extending beyond the perimeter of the absorbent pad layer so that the periphery of the dispersive layer adheres to the adhesive tape layer;
a plurality of radially oriented slits through the conductive layer, coincident with the first aperture in the adhesive tape layer, the slits and the first aperture forming a site at which a drug solution can be injected into the absorbent pad layer; and
an electrical contact attached to the conductive layer.

21. The iontophoresis electrode of claim 20 wherein the adhesive tape layer includes a sheet of adhesive tape.

22. The iontophoresis electrode of claim 21 wherein the adhesive tape layer includes a sheet of polyvinyl chloride foam.

23. The iontophoresis electrode of claim 22 wherein the adhesive tape layer includes a layer of medical grade acrylic pressure-sensitive adhesive.

24. The iontophoresis electrode of claim 20 wherein the conductive layer includes carbon loaded silicone rubber.

25. The iontophoresis electrode of claim 20 wherein the absorbent pad layer includes polyester fiber fill.

26. The iontophoresis electrode of claim 20 wherein the dispersive layer includes a sheet of filter paper.

27. The iontophoresis electrode of claim 26 wherein the sheet of filter paper includes a sheet of absorbent low-particle polyester-cellulose.

28. The iontophoresis electrode of claim 20 wherein the electrode includes more than one site for injecting the solution into the electrode.

29. The iontophoresis electrode of claim 20 and further comprising:
a removable protective layer that overlies the dispersive layer and the adhesive tape layer.

30. The iontophoresis electrode of claim 20 wherein the electrical contact includes a snap-type contact.

31. The iontophoresis electrode of claim 30 wherein the adhesive tape layer includes a second aperture and wherein the snap-type contact includes an eyelet and a stud positioned on opposite faces of the conductive layer, the eyelet extending through the second aperture in the adhesive tape layer, the stud having a post extending through the conductive layer for connection with the eyelet.

32. The iontophoresis electrode of claim 31 wherein the eyelet includes conductive material and the stud includes nonconductive material.

33. The iontophoresis electrode of claim 32 wherein the stud includes nonconductive plastic.

* * * * *